(12) United States Patent
Shan

(10) Patent No.: US 12,256,925 B2
(45) Date of Patent: Mar. 25, 2025

(54) CLOSURE DRIVING MECHANISM AND SURGICAL STAPLER

(71) Applicant: Touchstone International Medical Science Co., Ltd., Suzhou (CN)

(72) Inventor: Teng Shan, Suzhou (CN)

(73) Assignee: Touchstone International Medical Science Co., Ltd., Suzhou (CN)

( * ) Notice: Subject to any disclaimer, the term of this patent is extended or adjusted under 35 U.S.C. 154(b) by 615 days.

(21) Appl. No.: 17/634,785

(22) PCT Filed: Aug. 27, 2020

(86) PCT No.: PCT/CN2020/111794
§ 371 (c)(1),
(2) Date: Feb. 11, 2022

(87) PCT Pub. No.: WO2021/037155
PCT Pub. Date: Mar. 4, 2021

(65) Prior Publication Data
US 2022/0330938 A1 Oct. 20, 2022

(30) Foreign Application Priority Data

Aug. 29, 2019 (CN) .......................... 201910806818.5
Aug. 29, 2019 (CN) .......................... 201921425066.X

(51) Int. Cl.
*A61B 17/072* (2006.01)
*A61B 17/068* (2006.01)
(Continued)

(52) U.S. Cl.
CPC .......... *A61B 17/068* (2013.01); *A61B 17/072* (2013.01); *A61B 17/07207* (2013.01);
(Continued)

(58) Field of Classification Search
CPC ............ A61B 17/072; A61B 17/07207; A61B 17/068; A61B 17/115; A61B 17/105;
(Continued)

(56) References Cited

U.S. PATENT DOCUMENTS 10,172,619 B2 * 1/2019 Harris ................... A61B 17/105
10,194,913 B2 * 2/2019 Nalagatla ........... A61B 17/1155
(Continued)

FOREIGN PATENT DOCUMENTS

CN 104323809 A 2/2015
CN 105324086 A 2/2016
(Continued)

OTHER PUBLICATIONS

English Translation of International Search Report issued for International Patent Application No. PCT/CN2020/111794 on Mar. 4, 2021 (3 pages).
(Continued)

*Primary Examiner* — Scott A Smith
(74) *Attorney, Agent, or Firm* — Fox Rothschild LLP

(57) ABSTRACT

A closure driving mechanism and a surgical stapler are provided. The closure driving mechanism includes a first slider, a locking member, a closure driver and a pushing block, the first slider is connected to the closure driver and includes a first fitting portion, the locking member includes a second fitting portion and a first lifting portion connected to each other, the pushing block includes a second lifting portion located under the first lifting portion. When the head assembly is closed, the closure driver is locked by the locking member fitting with the first slider. After the stapler is fired and the pushing block is lifted, the locking member separates from the first slider. Therefore, the closure driver can move distally to open the head assembly.

13 Claims, 13 Drawing Sheets

(51) Int. Cl.
    *A61B 17/00* (2006.01)
    *A61B 17/115* (2006.01)
(52) U.S. Cl.
    CPC .............. *A61B 2017/00407* (2013.01); *A61B 2017/00477* (2013.01); *A61B 2017/07214* (2013.01); *A61B 17/115* (2013.01)
(58) Field of Classification Search
    CPC .......... A61B 2017/00022; A61B 2017/00473; A61B 2017/00477; A61B 2017/07214; A61B 2017/07271
    USPC ..... 227/19, 175.1, 176.1, 180.1; 606/1, 139, 606/219
    See application file for complete search history.

(56) References Cited

U.S. PATENT DOCUMENTS

| | | | |
|---|---|---|---|
| 10,307,163 B2* | 6/2019 | Moore | A61B 50/26 |
| 2009/0250502 A1 | 10/2009 | Milliman | |
| 2010/0264194 A1 | 10/2010 | Huang et al. | |
| 2015/0136833 A1 | 5/2015 | Shelton, IV et al. | |
| 2017/0027572 A1* | 2/2017 | Nalagatla | A61B 17/068 |

FOREIGN PATENT DOCUMENTS

| | | |
|---|---|---|
| CN | 207785223 U | 8/2018 |
| CN | 209107463 U | 7/2019 |
| CN | 210990510 U | 7/2020 |
| EP | 3123956 A2 | 2/2017 |
| JP | H09164144 A | 6/1997 |
| RU | 2627599 C2 | 8/2017 |

OTHER PUBLICATIONS

Extended European Search Report issued Oct. 26, 2022 for European Patent Application No. 20857628.0.

Japanese Notice of Reasons for Refusal issued on Feb. 24, 2023 for Japanese Patent Application No. 2022-512846 (4 pages).

* cited by examiner

CLOSURE DRIVING MECHANISM AND SURGICAL STAPLER

CROSS-REFERENCE TO RELATED APPLICATIONS

This application is based upon PCT patent application No. PCT/CN2020/111794, filed on Aug. 27, 2020, which claims priority to Chinese Patent Applications No. 201910806818.5, and No. 201921425066.X, filed on Aug. 29, 2019, the entire contents of which are incorporated herein by reference.

TECHNICAL FIELD

The present disclosure relates to medical instruments' technology, more particularly, to a closure driving mechanism and a surgical stapler.

BACKGROUND

Digestive tract disease is one of human diseases of high incidence. During treatment, a surgical stapler is widely used for suturing physiological tissues such as tissues in the digestive tract, instead of the manual operation by doctors. The surgical stapler is a common surgical instrument, and used for end-to-end anastomosis, or end-to-side anastomosis of the physiological tissues of esophagus, stomach, intestine, etc., in a way of axial internal stapling. During the process of anastomoses, two sections of tissues are accommodated in the stapler, and form a circular anastomotic stoma after firing the stapler, to rebuild a tissue channel.

In the prior art, the surgical stapler includes an instrument body, a firing handle rotatably connected to the instrument body and a head assembly cooperated with the instrument body. The head assembly includes a cartridge and an anvil located relative to each other. During the operation, the firing handle is actuated for a first time, a pulling sheet of the head assembly is pulled by a closure driving mechanism to move proximally, thereby closing the cartridge and the anvil. After the head assembly is closed, the firing handle is actuated again, the staples are pushed towards the tissues and form a closed shape at the anvil to suture the tissues. Meanwhile, the cutter moves towards a distal side of the staple to cut the tissues. In the present disclosure, the terms "distal side" and "proximal side" are used herein with reference to an operator manipulating the stapler. The term "proximal side" refers to a side closer to the operator, and the term "distal side" refers to a side away from the operator, that is, a side closer to the surgical site.

The traditional closure driving mechanism has a complex structure. The pulling sheet may move distally during the firing process of the stapler, affecting the closure stability between the cartridge and the anvil, thereby affecting the operation effect. Furthermore, after the stapler with the traditional closure driving mechanism is fired, the cartridge and the anvil are still closed. The operator needs to pull a cutter pushing rod back, to move the cutter back to its initial position along a cutter groove. If the cartridge and the anvil are still closed during the pulling process of the cutter, the cutter cannot return to its initial position smoothly, due to the resistance from the tissues between the cartridge and the anvil.

SUMMARY

To solve the problems in the prior art, the present disclosure provides a closure driving mechanism and a surgical stapler, wherein the position of a closure driver is locked by fitting cooperation between a locking member and a first slider when the head assembly is closed; after the stapler is fired, the locking member is lifted by a pushing block to separate from the first slider, allowing the closure driver to move to open the head assembly.

In the present disclosure, a closure driving mechanism used for a surgical stapler is provided, the surgical stapler includes a head assembly, the mechanism includes a first slider, a locking member, a closure driver and a pushing block, the first slider is connected to the closure driver and includes a first fitting portion, the locking member includes a second fitting portion and a first lifting portion connected to each other, the pushing block includes a second lifting portion located under the first lifting portion;

wherein, when the head assembly is closed, the first fitting portion is under and fits with the second fitting portion; when the pushing block is lifted upwards, the second lifting portion lifts the first lifting portion upwards, thereby moving the second fitting portion upwards to separate from the first fitting portion.

In some embodiments, in the initial state, the second lifting portion is separated from the first lifting portion.

In some embodiments, the closure driving mechanism further includes a firing handle and a pressing member; in an initial state, the first fitting portion and the pressing member are both located at a proximal side of the locking member;

when the firing handle is actuated in the initial state, the first slider moves distally, the first fitting portion is moved to be under the second fitting portion, the pressing member moves distally and presses the locking member downwards, the second fitting portion is moved downwards to fit with the first fitting portion, and the first slider moves the closure driver proximally to close the stapler.

In some embodiments, the closure driving mechanism further includes an actuating rod, the pressing member is provided on a distal side of the actuating rod, when the firing handle is actuated in the initial state, the firing handle drives the actuating rod to move distally.

In some embodiments, the locking member includes a second slider and a third slider, the second slider includes the second fitting portion and the first lifting portion; when the firing handle is actuated in the initial state, the pressing member presses the third slider downwards, and the third slider is driven to move the second slider downwards.

In some embodiments, a first biasing member is provided between the second slider and the third slider, the first biasing slider applies a downward biasing force to the second slider;

when the first fitting portion fits with the second fitting portion and the pushing block is lifted upwards, the second slider moves upwards relative to the third slider to deform the first biasing member.

In some embodiments, when the head assembly is closed, the second lifting portion is separated from the first lifting portion; or, when the head assembly is closed, the second lifting portion contacts the first lifting portion, while a force from the second lifting portion to the second slider is less than a force capable of deforming the first biasing member.

In some embodiments, an accommodating groove is provided in the third slider for housing the second slider.

In some embodiments, a second biasing member is provided between the pushing block and a housing of the stapler, and the second biasing member applies a downward biasing force to the pushing block;

when the pushing block is lifted upwards, the second biasing member is deformed.

In some embodiments, a third biasing member is provided at a proximal side of the closure driver, and the third biasing member applies a biasing force towards a distal side of the stapler.

In some embodiments, the pushing block further includes an operation portion, and a first side of the operation portion protrudes outside through a housing of the stapler.

In some embodiments, the second lifting portion is a lifting arm protruding from a second side of the operation portion.

In some embodiments, a fourth biasing member is provided between the locking member and a housing of the stapler, and the fourth biasing member applies an upward biasing force to the locking member.

In some embodiments, one of the first fitting portion and the second fitting portion is a boss, and the other one is a groove.

The present disclosure further provides a surgical stapler including the closure driving mechanism.

The closure driving mechanism and the surgical stapler have the following advantages.

The present disclosure provides a closure driving mechanism used for a surgical stapler. Before firing the stapler, and after the head assembly is closed by a closure driver, the position of the closure driver is locked by fitting cooperation between the locking member and the first slider, avoiding the pulling sheet moving distally during the firing process. After the stapler is fired and the head assembly needs to be opened, the pushing block is lifted to separate the locking member from the first slider, so that the locking member no longer locks the position of the closure driver, the closure drive is free to return to its initial position to open the cartridge and the anvil, then the cutter can be pulled back very smoothly.

BRIEF DESCRIPTION OF THE DRAWINGS

Embodiments of the present disclosure will now be described, by way of example only, with reference to the accompanying schematic drawings. Apparently, the following figures are only exemplary. For the skilled in the art, other figures can also be gotten according to the following figures without creative work.

DETAILED DESCRIPTION

Figure 1:
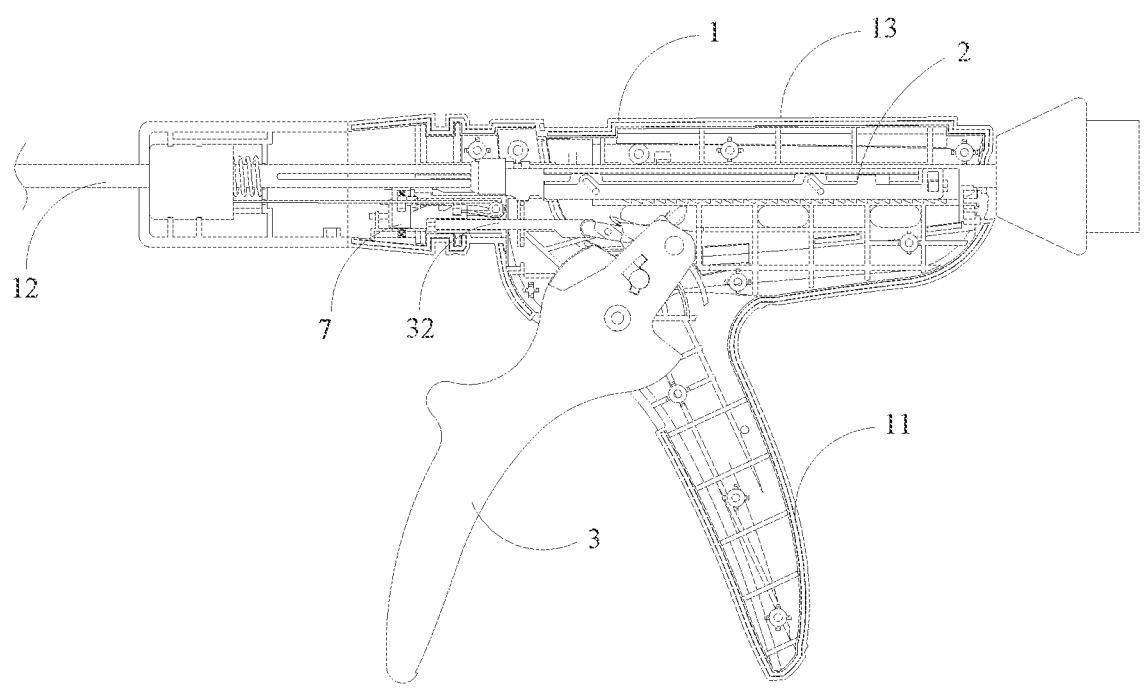
FIG. 1 is a structural schematic view of a part of a stapler in an initial state according to a first embodiment of the present disclosure.

Embodiments of the present disclosure will now be described, by way of example only, with reference to the accompanying schematic drawings according to embodiments of the present disclosure, to make the objective, technical proposal and advantages clearer. It should understand that the embodiment described are only a part of embodiments of the present disclosure, and are not intended to be a limitation to the protection scope of the present disclosure.

To solve the technical problem of the existing technology, the present disclosure provides a closure driving mechanism used for a surgical stapler and a surgical stapler including the closure driving mechanism. The stapler includes a head assembly and an instrument body, and a pulling sheet is provided in the instrument body for closing the head assembly. The closure driving mechanism includes a first slider, a locking member, a closure driver and a pushing block. The closure driver is connected to the pulling sheet to open and close the head assembly. In the present disclosure, the closure driver has a closed position and an open position. The head assembly is closed when the closure driver is in the closed position, and the head assembly is opened when the closure driver is in the open position. The first slider is connected to the closure driver and includes a first fitting portion. The locking member includes a second fitting portion and a first lifting portion connected to each other. The pushing block includes a second lifting portion located under the first lifting portion.

When the head assembly is closed, the first fitting portion of the first slider is under and fits with the second fitting portion of the locking member. Therefore, the closure driver is kept in the closed position by the locking member, the head assembly is kept closed and won't be accidently opened. After the stapler is fired and if the head assembly needs to be opened, the operator lifts the pushing block upwards, the second lifting portion of the pushing block lifts the first lifting portion of the locking member upwards. Then the second fitting portion connected to the first lifting portion is moved upwards and separated from the first fitting portion. Therefore, the locking member no longer locks the position of the first slider, thereby no longer locking the position of the closure driver connected to the first slider. The closure driver can move to the open position to open the head assembly. At this time, the cutter can be pulled back smoothly.

In the following, the structures of the closure driving mechanism and the stapler in specific embodiments are described combining FIGS. 1-13.

As shown in FIGS. 1-5, in the first embodiment of the present disclosure, the stapler includes an instrument body 1 and a head assembly (not shown in the drawings) located at a distal side of the instrument body 1. The instrument body 1 includes a housing 13 and a fixed handle 11. A pulling sheet 12 is located in the instrument body 1 and used for closing and opening the head assembly. The head assembly is opened when the pulling sheet 12 is in an initial state, and the head assembly is closed when the pulling sheet 12 moves proximally. Then the head assembly can be opened again when the pulling sheet 12 moves distally after the head assembly is closed. The closure driving mechanism includes a first slider 5, a locking member, a closure driver 83 and a pushing block 4. The first slider 5 is connected to the closure driver 83 and includes a first fitting portion. The locking member includes a second fitting portion and a first lifting portion 64 connected to each other. The pushing block 4 includes a second lifting portion 41 located under the first lifting portion 64.

Figure 2:
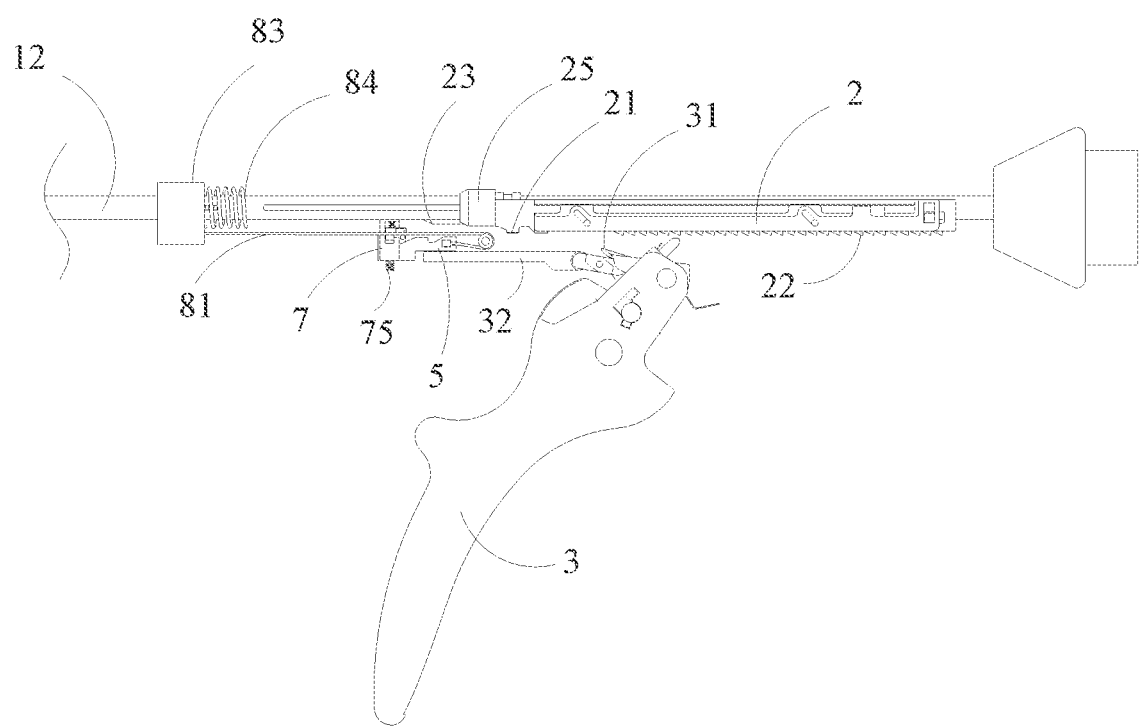
FIG. 2 is a structural schematic view of the stapler of FIG. 1 after a housing is removed.

In the present disclosure, the terms "distal side" and "proximal side" are used herein with reference to an operator manipulating the stapler. The term "proximal side" refers to a side closer to the operator, and the term "distal side" refers to a side away from the operator, that is, a side closer to the surgical site. The term "move distally" refers to moving towards a distal side of the stapler, and the term "move proximally" refers to moving towards a proximal side of the stapler. For example, as shown in FIGS. 1 and 2, the distal side of the instrument body 1 is a left side thereof, the proximal side of the instrument body 1 is a right side thereof, the distal side of the actuating rod 2 is a left side thereof, and the proximal side of the actuating rod 2 is a right side thereof. The terms "up", "upwards", "down" and "downwards" are used herein with reference to the actuating rod 2, wherein, the term "upwards" refers to a direction away from the gear 22, and the term "downwards" refers to a direction opposite to "upwards". For example, as shown in FIG. 1, the upward direction is a direction from a bottom end towards an up end.

In the embodiment, the first fitting portion of the first slider 5 is a first groove 51, the second fitting portion of the locking member is a boss 61. In another embodiment, the first fitting portion is a boss and the second fitting portion of the locking member is a groove.

Figure 3:
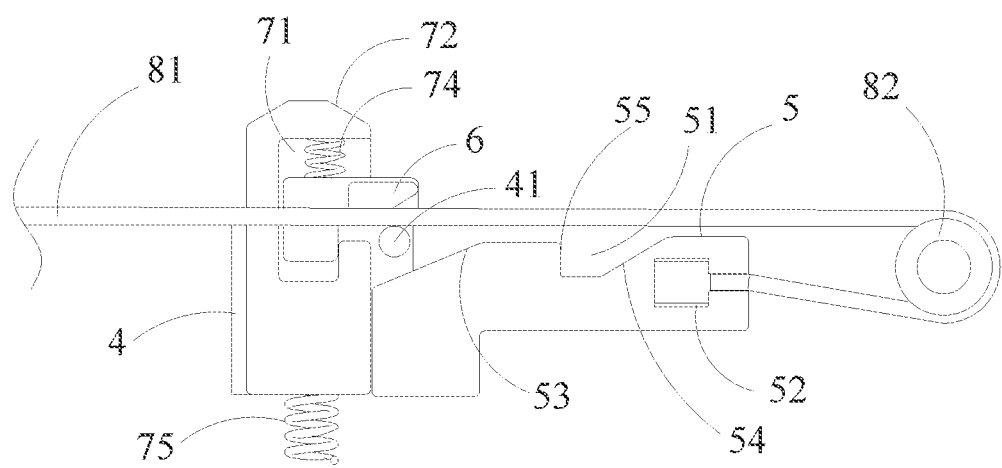
FIG. 3 is a schematic view of positions of a first slider and a locking member in the initial state according to the first embodiment of the present disclosure.
Figure 4:
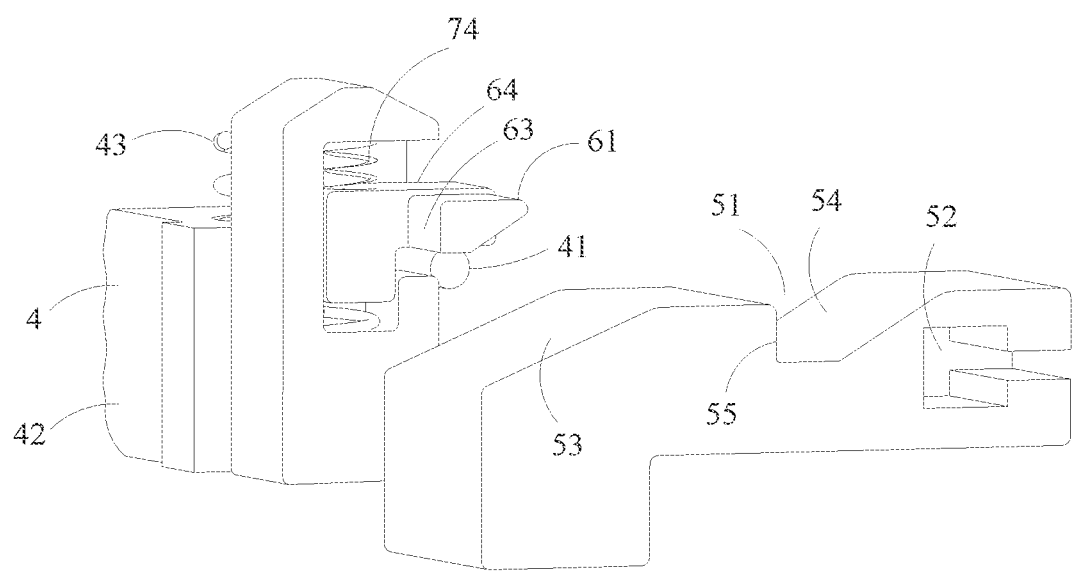
FIG. 4 is a stereogram of the first slider and the locking member in the initial state according to the first embodiment of the present disclosure.

As shown in FIG. 3 and FIG. 4, in the embodiment, the locking member includes a second slider 6 and a third slider 7. The third slider 7 is provided with an accommodating groove 71 for housing the second slider 6. The second slider 6 includes the boss 61 and the first lifting portion 64. A first biasing member is provided between the second slider 6 and the third slider 7, and the first biasing member applies a downward biasing force to the second slider 6. A fourth biasing member is provided between the third slider 7 and the housing of the stapler, and the fourth biasing member applies an upward biasing force to the third slider 7. In the embodiment, the first biasing member is a first compression spring 74 disposed between an inner wall of the accommodating groove 71 and the second slider 6. The fourth biasing member is a fourth compression spring 75 disposed under the third slider 7. In alternative embodiments, the first biasing member can be a tension spring, an elastic metal sheet or other kinds of elastic structures, and the fourth biasing member can be a tension spring, an elastic metal sheet or other kinds of elastic structures.

Figure 5:
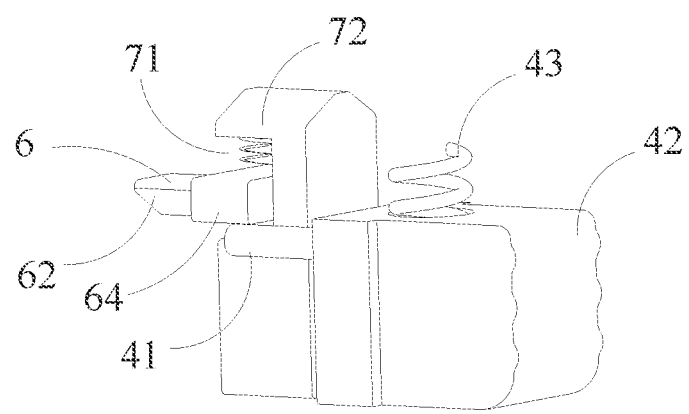
FIG. 5 is a structural schematic view of the cooperation between the locking member and the pushing block according to the first embodiment of the present disclosure.
Figure 10:
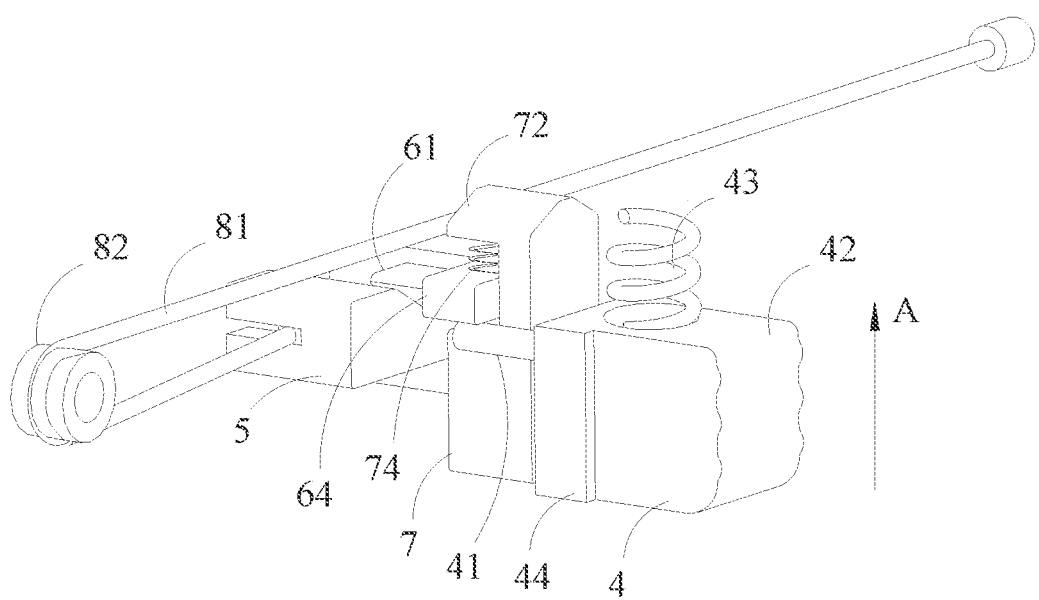
FIG. 10 is a structural schematic view of the cooperation between the locking member, the pushing block and the first slider when the head assembly is closed according to the first embodiment of the present disclosure.
Figure 11:
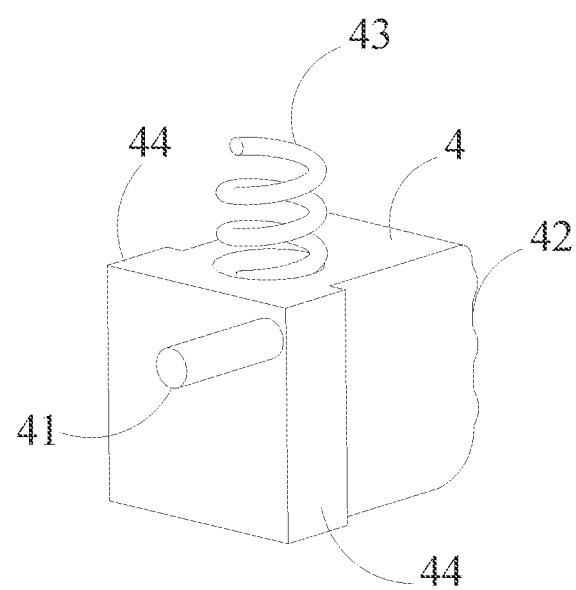
FIG. 11 is a structural schematic view of the pushing block when the head assembly is closed according to the first embodiment of the present disclosure.

As shown in FIG. 5, the pushing block 4 further includes an operation portion 42, the second lifting portion 41 of the pushing block 4 is a lifting arm protruding from a second side of the operation portion 42. A first side of the operation portion 42 protrudes outside through the housing of the stapler, so that the doctor can directly operate the operation portion 42 outside the housing. A second biasing member is provided between the pushing block 4 and the housing of the stapler, and the second biasing member applies a downward biasing force to the pushing block 4. In the embodiment, the second biasing member is a second compression spring 43 located above the pushing block 4. In alternative embodiments, the second biasing member can be a tension spring, an elastic metal sheet or other kinds of elastic structures. As shown in FIG. 10 and FIG. 11, the pushing block 4 is provided with a first guiding portion 44, and the housing 13 (shown in FIG. 1) is provided with a second guiding portion (not shown in the drawings) cooperated with the first guiding portion 44. One of the first guiding portion 44 and the second guiding portion is a boss, and the other one is a groove. With the mutual guidance between the first guiding portion 44 and the second guiding portion, the pushing block 4 is movable along an extension direction of the second compression spring 43. That is, as shown in FIG. 10, with the mutual guidance between the first guiding portion 44 and the second guiding portion, the pushing block 4 is movable along direction A or a direction opposite to direction A. A bottom side of the pushing block 4, that is, a side of the pushing block 4 away from the second compression spring 43, contacts the housing 13, so that the pushing block 4 cannot separate from the housing.

Furthermore, a third biasing member is provided at a proximal side of the closure driver 83, and the third biasing member applies a biasing force towards the distal side of the stapler to the closure driver 83. In the embodiment, the third biasing member is a third compression spring 84 located at the proximal side of the closure driver 83. In alternative embodiments, the third biasing member can be a tension spring, an elastic metal sheet or other kinds of elastic structures.

The first slider 5 is connected to the closure driver 83 through a turning assembly. The turning assembly includes a support member fixed to the housing and a rope 81. In the embodiment, the support member is a pulley 82 to decrease the resistance when the rope 81 moves. The pulley 82 is located at a proximal side of the first slider 5. The rope 81 is arranged outside the pulley 82, and connected between the first slider 5 and the closure driver 83. In the embodiment, each of two ends of the rope 81 is provided with a fixed end. A second groove 52 can be provided at the proximal side of the first slider 5 for removably mounting one fixed end of the rope 81. The other fixed end of the rope 81 is removably connected to the closure driver 83. With the structures of the rope 81 and the pulley 82, the movement of the first slider 5 results in a driving force in a reverse direction to the closure driver 83.

In the embodiment, the closure driving mechanism further includes a firing handle 3 and a pressing member. The pressing member is a ledge 23 provided on a distal side of the actuating rod 2. In the initial state, the first groove 51 of the first slider 5 is in its initial position, which is at a proximal side of the boss 61 of the locking member, the pressing member is in its initial position, which is at a proximal side of the locking member.

Figure 6:
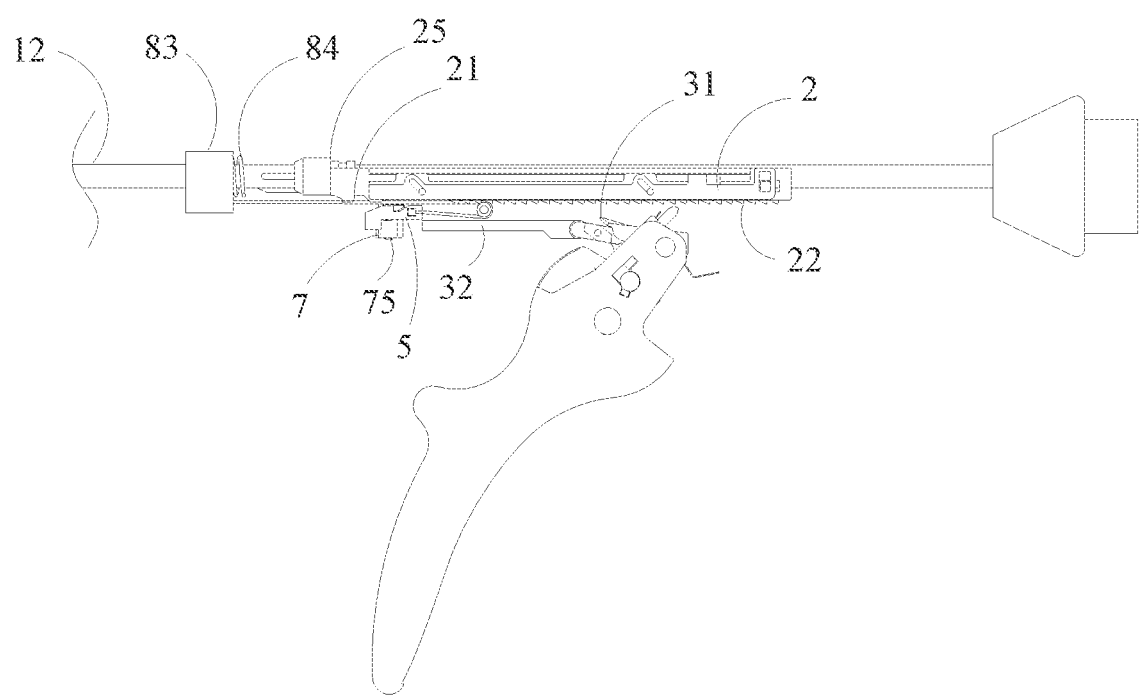
FIG. 6 is a structural schematic view of a part of the stapler when the head assembly is closed according to the first embodiment of the present disclosure.

As shown in FIGS. 6-11, when the firing handle 3 is actuated in the initial state, the rotation of the firing handle 3 drives a connecting rod 32 to move distally, so that the connecting rod 32 pushes the first slider 5 to move distally, then the first groove 51 moves to be under the boss 61. The turning assembly turns the distal movement of the first slider 5 to a proximal movement of the closure driver 83. Therefore, the closure driver 83 moves from the open position to the closed position, to drive the pulling sheet 12 to move proximally, thereby closing the head assembly of the stapler. As shown in FIG. 6, the third compression spring 84 is compressed to deform by the closure driver 83.

Figure 7:
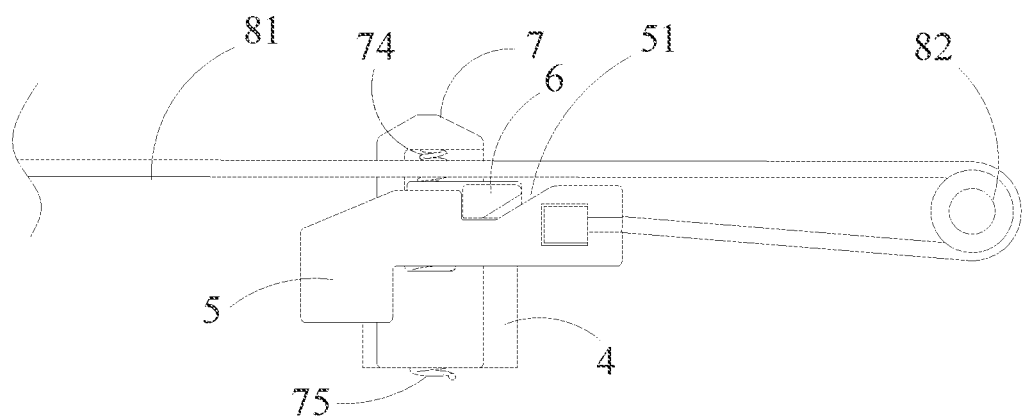
FIG. 7 is a structural schematic view of the first slider and the locking member when the head assembly is closed according to the first embodiment of the present disclosure.

Simultaneously, when the firing handle 3 is actuated to rotate in the initial state, a claw 31 on the firing handle 3 contacts a pushing tooth 21 on the actuating rod 2, and pushes the pushing tooth 21 distally. After the actuating rod 2 moves distally until the ledge 23 contacts the third slider 7, the third slider 7 is pressed downwards by the ledge 23 and drives the second slider 6 to move downwards. At this time, the boss 61 of the second slider 6 fits with the first groove 51 of the first slider 5, to block the first slider 5 from moving proximally, thereby keeping the closure driver 83 in the closed position. Therefore, the closure stability of the head assembly is improved. As shown in FIG. 6 and FIG. 7, as the ledge 23 presses the third slider 7 downwards, the third slider 7 compresses the fourth compression spring 75 to deform. Preferably, in the initial state, a distance exists between the first lifting portion 64 and the second lifting portion 41, that is, the first lifting portion 64 is separated from the second lifting portion 41. As shown in FIG. 10 and FIG. 11, when the firing handle 3 is actuated for closing the head assembly, the boss 61 of the second slider 6 fits with the first groove 51 of the first slider 5. At this time, a small distance exists between the first lifting portion 64 and the second lifting portion 41, that is, the first lifting portion 64 is separated from the second lifting portion 41. Furthermore, the second lifting portion 41 can contact and lift the first lifting portion 64 when the pushing block 4 moves upwards. In an alternative embodiment, when the firing handle 3 is actuated for closing the head assembly, the boss 61 of the second slider 6 fits with the first groove 51 of the first slider 5, and the second lifting portion 41 contacts the first lifting portion 64. However, the force applies from the second lifting portion 41 to the first lifting portion 64 is not big enough to deform the first compression spring 74. Therefore, when the pushing block 4 is not lifted, the second lifting portion 41 cannot lift the boss 61 to separate from the first groove 51 of the first slider 5, to ensure the closure stability of the head assembly.

Figure 8:
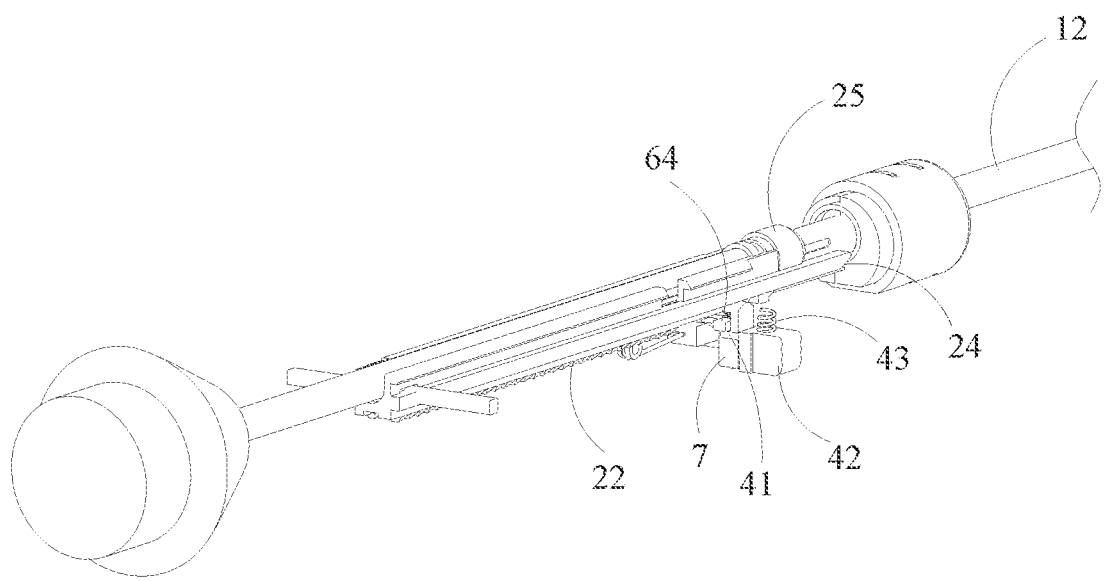
FIG. 8 is a stereogram of the closure driving mechanism when the head assembly is closed according to the first embodiment of the present disclosure.

As shown in FIG. 8, a distal side surface of the ledge 23 is a first inclined surface 24 of the ledge 23, which inclines upwards from a proximal side to a distal side thereof. A proximal side surface of the third slider 7 is a first inclined surface 72 of the third slider 7, which cooperates with the first inclined surface 24 of the ledge 23. With the mutual guidance between the first inclined surface 24 and the first inclined surface 72, the ledge 23 can contact and press the third slider 7 more smoothly when moving distally.

Figure 9:
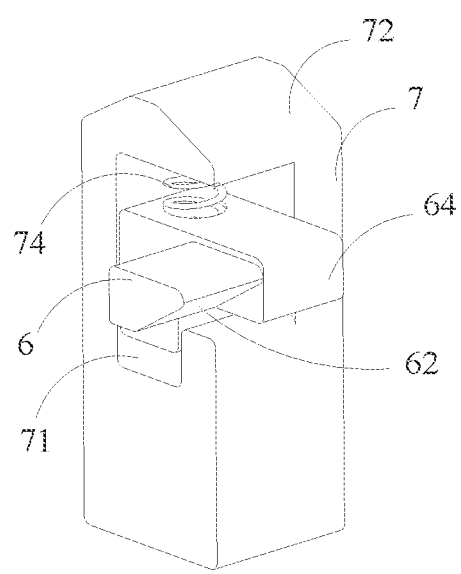
FIG. 9 is a structural schematic view of the locking member when the head assembly is closed according to the first embodiment of the present disclosure.

As shown in FIG. 4 and FIG. 9, a distal side surface of the first slider 5 is a first inclined surface 53 of the first slider 5, which inclines upwards from a distal side to a proximal side thereof, that is, inclines downwards from the proximal side to the distal side thereof. A proximal side surface of the boss 61 is a boss inclined surface 62, which cooperates with the first inclined surface 53 of the first slider 5. With the mutual guidance between the first inclined surface 53 and the boss inclined surface 62, the boss 61 of the second slider 6 can smoothly enter the first groove 51 of the first slider 5. Furthermore, the first groove 51 has a shape corresponding to the shape of the boss 61. That is, the proximal side surface of the first groove 51 is a second inclined surface 54 of the first slider 5, which inclines upwards from a distal side to a proximal side thereof.

A distal side surface of the first groove 51 is a first blocking surface 55. Correspondingly, a distal side surface of the boss 61 is a second blocking surface 63. The first blocking surface 55 and the second blocking surface 63 are both vertical surfaces. The first blocking surface 55 and the second blocking surface 63 are arranged with an interval therebetween when they are in their initial positions. With the cooperation between the first blocking surface 55 and the second blocking surface 63, the boss 61 prevents the first slider 5 from moving proximally when the boss 61 is inserted in the first groove 51.

After the head assembly is closed, the state of the stapler is shown in FIG. 6. When the firing handle 3 is actuated to rotate for a second time in the state after the head assembly is closed, the claw 31 contacts and pushes the rack 22 to move the actuating rod 2 distally. The actuating rod 2 is provided with a firing member 25. The firing member 25 is capable of firing the stapler to suture and cut tissues when moving distally. During the firing process of the stapler, under the pressure from the ledge 23, the boss 61 of the second slider 6 is kept in the first groove 51 of the first slider 5, thereby improving the closure stability of the head assembly during the firing process of the stapler.

After the stapler is fired, if the head assembly needs to be opened to separate the cartridge and the anvil, the locking member needs to separate from the first slider 5. That is, in the embodiment, the boss 61 of the second slider 6 needs to separate from the first groove 51 of the first slider 5.

Figure 12:
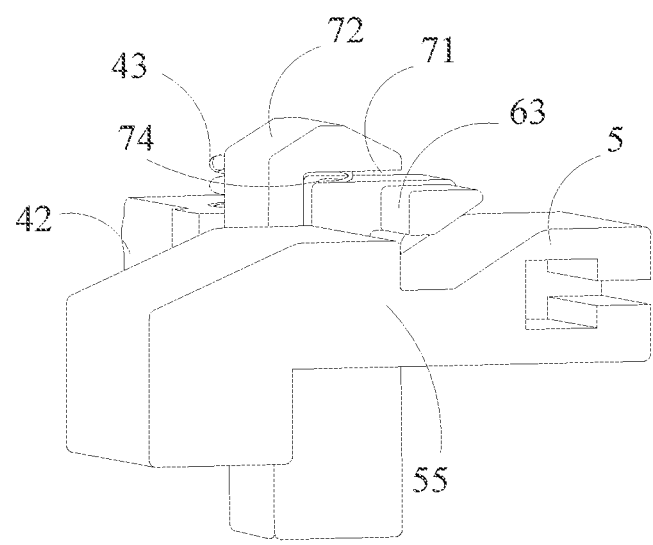
FIG. 12 is a stereogram of the cooperation between the locking member and the first slider when the pushing block is lifted according to the first embodiment of the present disclosure.
Figure 13:
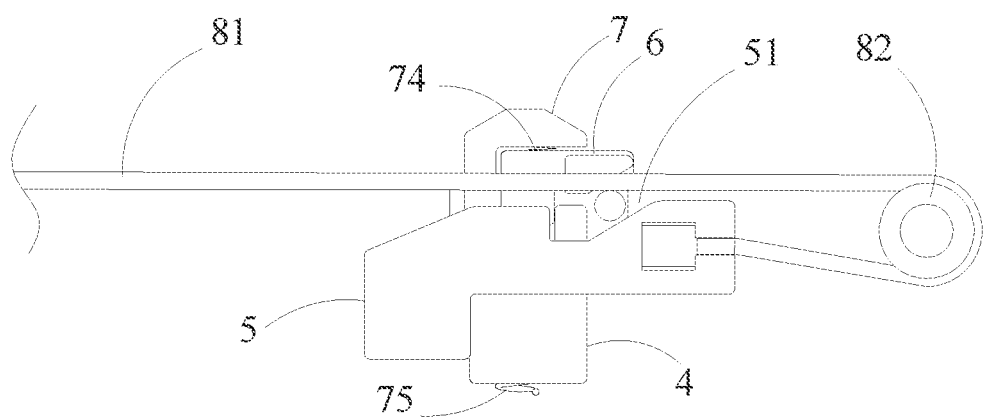
FIG. 13 is a structural schematic view of the cooperation between the locking member and the first slider when the pushing block is lifted according to the first embodiment of the present disclosure.

When the head assembly is closed, the closure driving mechanism is in the state shown in FIG. 10. At this time, if the doctor lifts the operation portion 42 of the pushing block 4 along the direction A shown in FIG. 10, the pushing block 4 moves upwards. Therefore, the second lifting portion 41 lifts the first lifting portion 64 to move the second slider 6 upwards. As shown in FIG. 12 and FIG. 13, when the second slider 6 is lifted by the pushing block 4, as the first slider 7 is kept at a stable height under the pressure from the ledge 23, the second slider 6 has an upward movement trend relative to the first slider 7 to deform the first compression spring 74. Then the boss 61 of the second slider 6 moves upwards to separate from the first groove 51. Simultaneously, during the lifting process, the pushing block 4 compresses the second compression spring 43 to deform, and the second slider 6 is lifted upwards by the pushing block 4 to separate the boss 61 of the second slider 6 from the first groove 51. As shown in FIG. 13, after the first slider 5 is no longer locked by the second slider 6, the closure driver 83 drives the rope 81 to move distally under the distal return force of the third compression spring 84, and the closure driver 83 drives the second slider 6 to move proximally under the turning function of the pulley 82. At this time, the closure driver 83 drives the pulling sheet 12 to move distally, to open the head assembly of the stapler. The anvil and the cartridge are separated to release the tissues therebetween and the cutter can be pulled back more smoothly.

FIGS. 1-13 only show the structure of the closure driving mechanism according to a specific embodiment of the present disclosure. The structure of the closure driving mechanism may have some variations that are all included in the protection scope of the present disclosure. For example, instead of providing the accommodating groove housing the second slider 6 in the third slider 7, the third slider 7 can be provided with a guiding groove, in which a part of the second slider 6 is inserted. Furthermore, an elastic member can be provided in the guiding groove. Therefore, the second slider 6 can be moved downwards by the third slider 7 when the third slider 7 moves downwards, and the second slider 6 has an upward movement trend relative to the third slider 7 when the third slider 7 stands still. The second lifting portion of the pushing block 4 can be a bump, a round platform or other structures instead of the lifting arm. The pressing member can be the firing member 25 for pressing the third slider 7 instead of the ledge on the actuating rod 2, or the actuating rod 2 can be provided with a bump as the pressing member, and the bump is capable of moving distally when the firing handle 3 is actuated.

The closure driving mechanism and the surgical stapler have the following advantages.

The present disclosure provides a closure driving mechanism used for a surgical stapler. Before firing the stapler, and after the head assembly is closed by a closure driver, the position of the closure driver is locked by fitting cooperation between the locking member and the first slider, avoiding the pulling sheet moving distally during the firing process. After the stapler is fired and the head assembly needs to be opened, the pushing block is lifted to separate the locking member from the first slider, so that the locking member no longer locks the position of the closure driver, the closure drive is free to return to its initial position to open the cartridge and the anvil, then the cutter can be pulled back very smoothly.

The above is a detailed description of the present disclosure in connection with the specific preferred embodiments, and the specific embodiments of the present disclosure are not limited to the description. Modifications and substitutions can be made without departing from the spirit and scope of the present disclosure.

What is claimed is:

1. A closure driving mechanism used for a surgical stapler having a head assembly, wherein the mechanism comprises a first slider, a locking member, a closure driver, a pushing block, a firing handle and a pressing member, the first slider is connected to the closure driver and comprises a first fitting portion, the locking member comprises a second fitting portion and a first lifting portion connected to each other, the pushing block comprises a second lifting portion located under the first lifting portion; one of the first fitting portion and the second fitting portion is a boss, and the other one is a groove; wherein in an initial state, the first fitting portion is located at a proximal side of the second fitting portion, and the pressing member is located at a proximal side of the locking member;

wherein, when the firing handle is actuated in the initial state, the first slider moves distally, the first fitting portion is moved to be under the second fitting portion, the pressing member moves distally and presses the locking member downwards, the second fitting portion is moved downwards to fit with the first fitting portion, and the first slider moves the closure driver proximally to close the stapler, therefore, when the head assembly is closed, the first fitting portion is under and fits with the second fitting portion; when the pushing block is lifted upwards, the second lifting portion lifts the first lifting portion upwards, thereby moving the second fitting portion upwards to separate from the first fitting portion.

2. The closure driving mechanism of claim 1, wherein, in the initial state, the second lifting portion is separated from the first lifting portion.

3. The closure driving mechanism of claim 1, wherein, the closure driving mechanism further comprises an actuating rod, the pressing member is provided on a distal side of the actuating rod; when the firing handle is actuated in the initial state, the firing handle drives the actuating rod to move distally.

4. The closure driving mechanism of claim 1, wherein, the locking member comprises a second slider and a third slider, the second slider comprises the second fitting portion and the first lifting portion; when the firing handle is actuated in the initial state, the pressing member presses the third slider downwards, and the third slider is driven to move the second slider downwards.

5. The closure driving mechanism of claim 4, wherein, a first biasing member is provided between the second slider and the third slider, the first-biasing member applies a downward biasing force to the second slider;

when the first fitting portion fits with the second fitting portion and the pushing block is lifted upwards, the second slider moves upwards relative to the third slider to deform the first biasing member.

6. The closure driving mechanism of claim 5, wherein, when the head assembly is closed, the second lifting portion is separated from the first lifting portion; or, when the head assembly is closed, the second lifting portion contacts the first lifting portion, while a force from the second lifting portion to the second slider is less than a force capable of deforming the biasing member.

7. The closure driving mechanism of claim 4, wherein, an accommodating groove is provided in the third slider for housing the second slider.

8. The closure driving mechanism of claim 1, wherein, a biasing member is provided at a proximal side of the closure driver, the biasing member applies a biasing force towards a distal side of the stapler to the closure driver.

9. A surgical stapler comprising a closure driving mechanism and a head assembly, wherein the closure driving mechanism comprises a first slider, a locking member, a closure driver, a pushing block, a firing handle and a pressing member, the first slider is connected to the closure driver and comprises a first fitting portion, the locking member comprises a second fitting portion and a first lifting portion connected to each other, the pushing block comprises a second lifting portion located under the first lifting portion; one of the first fitting portion and the second fitting portion is a boss, and the other one is a groove; wherein in an initial state, the first fitting portion is located at a proximal side of the second fitting portion, and the pressing member is located at a proximal side of the locking member;

wherein, when the firing handle is actuated in the initial state, the first slider moves distally, the first fitting portion is moved to be under the second fitting portion, the pressing member moves distally and presses the locking member downwards, the second fitting portion is moved downwards to fit with the first fitting portion, and the first slider moves the closure driver proximally to close the stapler, therefore, when the head assembly is closed, the first fitting portion is under and fits with the second fitting portion; wherein, when the pushing block is lifted upwards, the second lifting portion lifts the first lifting portion upwards, therefore the first lifting portion moves the second fitting portion upwards to separate from the first fitting portion.

10. The surgical stapler of claim 9, wherein, a biasing member is provided between the pushing block and a housing of the stapler, the biasing member applies a downward biasing force to the pushing block; when the pushing block is lifted upwards, the biasing member is deformed.

11. The surgical stapler of claim 9, wherein the pushing block further comprises an operation portion, a first side of the operation portion protrudes outside through a housing of the stapler.

12. The surgical stapler of claim 11, wherein the second lifting portion is a lifting arm protruding from a second side of the operation portion.

13. The surgical stapler of claim 9, wherein a biasing member is provided between the locking member and a housing of the stapler, the biasing member applies an upward biasing force to the locking member.

\* \* \* \* \*